United States Patent [19]

Lang et al.

[11] Patent Number: 4,888,026
[45] Date of Patent: Dec. 19, 1989

[54] USE OF HYDROXYNAPHTHOQUINONES FOR DYEING HUMAN KERATIN FIBRES

[75] Inventors: Gérard Lang, Saint-Gratien; Serge Forestier, Claye-Souilly; Michel Hocquaux; Jean-Francois Grollier, both of Paris; Georges Rosenbaum, Asnieres, all of France

[73] Assignee: L'Oreal, Paris, France

[21] Appl. No.: 689,011

[22] Filed: Dec. 28, 1984

Related U.S. Application Data

[63] Continuation of Ser. No. 445,705, Dec. 1, 1982, abandoned.

[30] Foreign Application Priority Data

Dec. 2, 1981 [LU] Luxembourg ............... 83806

[51] Int. Cl.$^4$ .................................. A61K 7/13
[52] U.S. Cl. ............................... 8/405; 8/428
[58] Field of Search ........................ 8/405, 428

[56] References Cited

U.S. PATENT DOCUMENTS

| | | | |
|---|---|---|---|
| 3,041,244 | 6/1962 | Feit ........................ | 8/663 |
| 3,516,778 | 6/1970 | Brunner .................... | 8/405 |
| 4,358,286 | 11/1982 | Grollier et al. .......... | 8/428 |

FOREIGN PATENT DOCUMENTS

| | | | |
|---|---|---|---|
| 2473310 | 7/1981 | France ..................... | 8/405 |
| 889813 | 2/1962 | United Kingdom . | |
| 1502275 | 3/1978 | United Kingdom . | |
| 2065177 | 6/1981 | United Kingdom ........... | 8/405 |

OTHER PUBLICATIONS

Edited by E. H. Rodd, "Chemistry of Carbon Compounds", 1956, pp. 1318–1323, 1400.
R. H. Thomson, "Naturally Occurring Quinones", 1957, pp. 55–60, 73–75, 100–102, 109–110, 125, 128–132, 135–140.
John F. Corbett, "The Chemistry of Synthetic Dyes", 1971, pp. 475–483.
Chemical Abstracts, vol. 87 (1977), 153693z, p. 84.
Abstract of Japanese Patent Appln. No. 54-111594.

*Primary Examiner*—Douglas W. Robinson
*Attorney, Agent, or Firm*—Fleit, Jacobson, Cohn, Price, Holman & Stern

[57] ABSTRACT

The use in dyeing human keratin fibres, especially human hair, of 2-hydroxy-1,4-naphthoquinones of the formula:

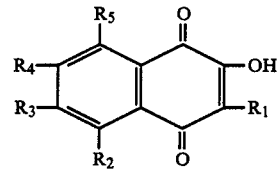

in which $R_1$ denotes a hydrogen or halogen atom, or a hydroxy, alkoxy, nitro, alkyl or acyl group, and $R_2$, $R_3$, $R_4$ and $R_5$ independently of one another denote hydrogen or a hydroxyl, alkoxy, alkyl or acyl group, such that at least one of the substituents $R_1$ to $R_5$ is other than hydrogen, and if $R_1$, $R_3$ and $R_4$ denote hydrogen, $R_2$ and $R_5$ cannot simultaneously denote hydroxyl is described.

16 Claims, No Drawings

USE OF HYDROXYNAPHTHOQUINONES FOR DYEING HUMAN KERATIN FIBRES

This application is a continuation of Ser. No. 445,705, filed Dec. 1, 1982, now abandoned.

The present invention relates to the use of 2-hydroxynaphthoquinone derivatives for dyeing human keratin fibres, and in particular hair, and to the processes and dyeing compositions in which these dyestuffs are employed.

Numerous direct dyestuffs, such as, in particular, triarylmethane dyestuffs, nitro derivatives of the benzene series, indoamines, aminoanthraquinones, xanthenes, acridines and azo dyestuffs, are commonly used in the field of hair dyeing.

Naphthoquinone dyestuffs, such as, in particular, certain hydroxynaphthoquinones, have also been used for this purpose. Thus, henna has been used since ancient times in the form of a poultice obtained by diluting with water a ground mass of leaves originating from the shrub *Lawsonia inermis*, and it has been known for a long time that the dyeing principle of henna is in fact 2-hydroxy-1,4-naphthoquinone, which is commonly called lawsone.

Walnut hulls have also been used traditionally for hair dyeing, although this practice is less widespread than the use of henna. As is also known, the dyeing principle of walnut hulls is 5-hydroxy-1,4-naphthoquinone, which is commonly called juglone. It is known that these preparations are sensitive to oxidation.

A few attempts have also been made to dye using 5,8-dihydroxynaphthoquinone, which is commonly called naphthazarine. However, the very low solubility of this product makes it necessary to use specific solubilising agents, and the dyeing results obtained remain mediocre.

We have therefore sought other hydroxynaphthoquinones which might possess a good tinctorial strength and a low sensitivity to oxidation.

We have discovered, according to the present invention, that a particular class of 2-hydroxyl-1,4-naphthoquinones makes it possible to achieve this result and, in addition, has a good stability to pH variations and can be used under the conditions used for dyeing human hair.

The dyestuffs used in the present invention have a high tinctorial strength, a low sensitivity to oxidation and a low sensitivity to pH variations, in particular in the case of red colorations, and they make it possible to obtain a very wide range of colours.

These dyestuffs generally have a good affinity, which makes them particularly suitable for dyeing human hair. They also have a good resistance to light, washing, weather and perspiration.

The present invention thus relates to the use of a new class of 2-hydroxy-1,4-naphthoquinones for dyeing human keratin fibres. The present invention provides dyeing processes in which these dyestuffs are employed, and dyeing compositions in which they are present.

The 2-hydroxy-1,4-naphthoquinones used according to the invention correspond to the general formula:

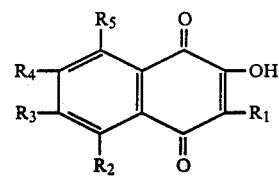

in which $R_1$ denotes a hydrogen atom, a hydroxyl, alkoxy or nitro group, a halogen atom or an alkyl or acyl group, and $R_2$, $R_3$, $R_4$ and $R_5$ independently of one another denote hydrogen or a hydroxyl, alkoxy, alkyl or acyl group, at least one of the substituents $R_1$ to $R_5$ being different from hydrogen, and if $R_1$, $R_3$ and $R_4$ denote hydrogen, $R_2$ and $R_5$ cannot simultaneously denote hydroxyl.

Preferred $R_1$ radicals include hydrogen, hydroxyl, methyl, ethyl, methoxy, acetyl and nitro as well as bromo while preferred $R_2$ to $R_5$ radicals include hydrogen, hydroxy and methoxy as well as ethyl and acetyl.

In the formula given above, the alkyl and alkoxy groups generally denote groups containing from 1 to 4 carbon atoms and the acyl group is a group preferably containing from 2 to 4 carbon atoms.

The dyestuffs which are more particularly preferred according to the invention are the following compounds: 2,3-dihydroxy-1,4-naphthoquinone, 2,5-dihydroxy-1,4-naphthoquinone, 2,6-dihydroxy-1,4-naphthoquinone, 2,7-dihydroxy-1,4-naphthoquinone, 2,8-dihydroxy-1,4-naphthoquinone, 2,5,7-trihydroxy-1,4-naphthoquinone, 2,6,7-trihydroxy-1,4-naphthoquinone, 2-hydroxy-3-methoxy-1,4-naphthoquinone, 1-hydroxy-3-methoxy-1,4-naphthoquinone, 2-hydroxy-6-methoxy-1,4-naphthoquinone, 2-hydroxy-7-methoxy-1,4-naphthoquinone, 2-hydroxy-8-methoxy-1,4-naphthoquinone, 2,3,5-trihydroxy-1,4-naphthoquinone, 2,3,5,8-tetrahydroxy-1,4-naphthoquinone, 2,3-dihydroxy-5-methoxy-1,4-naphthoquinone, 2,3-dihydroxy-7-methoxy-1,4-naphthoquinone, 2,8-dihydroxy-3-methyl-1,4-naphthoquinone, 2-hydroxy-3-nitro-7-methoxy-1,4-naphthoquinone and 2-hydroxy-3-methyl-1,4-naphthoquinone.

Other dyestuffs which are of value within the scope of the invention are the following dyestuffs: 2,5,6,7-tetrahydroxy-1,4-naphthoquinone, 2,5,7,8-tetrahydroxy-1,4-naphthoquinone, 2,5,6,7,8-pentahydroxy-1,4-naphthoquinone, 2-hydroxy-5,8-dimethoxy-1,4-naphthoquinone, 2-hydroxy-5,6,7-trimethoxy-1,4-naphthoquinone, 2-hydroxy-5,7,8-trimethoxy-1,4-naphthoquinone, 2-hydroxy-5,6,7,8-tetramethoxy-1,4-naphthoquinone, 2-hydroxy-3-bromo-1,4-naphthoquinone, 2,5,8-trihydroxy-6-ethyl-1,4-naphthoquinone, 2,5,7-trihydroxy-6-acetyl-1,4-naphthoquinone, 2,5,8-trihydroxy-6-acetyl-1,4-naphthoquinone and 2,5,7,8-tetrahydroxy-3-acetyl-1,4-naphthoquinone.

Numerous of the dyestuffs of formula (I) are of natural origin and can be obtained from vegetable or animal substances. By way of indication, Table (I) below gives dyestuffs of natural origin which correspond to the formula (I).

TABLE 1

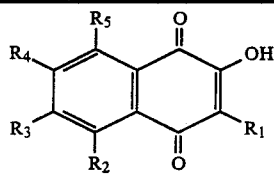

| COMMON NAME | R1 | R2 | R3 | R4 | R5 | ORIGIN |
|---|---|---|---|---|---|---|
| PHTIOCOL | CH3 | H | H | H | H | *MYCOBACTERIUM TUBERCULOSIS* |
| — | H | OH | H | H | H | *VERTICILLIUM DAHLIAE* |
| — | H | OH | C2H5 | H | H | " |
| — | H | H | H | H | OH | " |
| DROSERONE | CH3 | H | H | H | OH | *DROSERA WHIHAKAERI* |
| DROSERONE METHYL ETHER | CH3 | H | H | H | OCH3 | *DIOSPYROS MELANOXYLON* |
| FLAVIOLINE | H | OH | H | OH | H | *ASPERGILLUS CITRICUS* |
| — | H | OH | COCH3 | OH | H | ECHINODERMATA Spp. |
| HYDROXYDROSERONE | CH3 | OH | H | H | OH | DROSERA Spp. |
| — | C2H5 | OH | H | H | OH | ECHINODERMATA Spp. |
| — | COCH3 | OH | H | H | OH | " |
| — | H | OH | C2H5 | H | OH | " |
| — | H | OH | COCH3 | H | OH | " |
| SPINOCHROME B | OH | OH | H | OH | H | ECHINODERMATA Spp. |
| — | OH | OH | C2H5 | OH | H | " |
| — | OH | OH | COCH3 | OH | H | " |
| CORDEAUXIONE | OCH3 | OH | CH3 | COCH3 | OH | *CORDEAUXIA EDULIS* |
| — | C2H5 | OH | OH | OH | H | ECHINODERMATA Spp. |
| SPINOCHROME S | COCH3 | OH | OH | OH | H | " |
| MOMPAINE | H | OH | H | OH | OH | *HELICOBASIDIUM MOMPA* |
| — | C2H5 | OH | H | OH | OH | ECHINODERMATA Spp. |
| SPINOCHROME A | COCH3 | OH | H | OH | OH | " |
| — | COCH3 | OH | H | OCH3 | OH | " |
| SPINOCHROME D | OH | OH | OH | H | OH | " |
| ECHINOCHROME A | OH | OH | OH | C2H5 | OH | " |
| SPINOCHROME C | COCH3 | OH | OH | OH | OH | " |
| — | OCH3 | OH | OH | C2H5 | OH | " |
| — | OCH3 | OH | C2H5 | OH | OH | " |
| SPINOCHROME E | OH | OH | OH | OH | OH | ECHINODERMATA Spp. |
| NAMAKOCHROME | OH | OH | OH | OCH3 | OH | " |
| — | OCH3 | OH | OH | OCH3 | OH | " |

The dyestuffs used in the present invention can be used either in the form of products obtained by synthesis, or, if appropriate, in the form of products obtained from the organisms which produce them or the plants in which they are present. In the latter case, the products can be used either in the form of extracts or in the form of homogenised masses of all or part of these organisms or plants.

The dyeing compositions for human keratin fibres, according to the invention, are essentially characterised in that they contain at least one dyestuff corresponding to the formula (I) above, in a cosmetically acceptable medium.

The dyestuffs are preferably present in these compositions in an amount from 0.01 to 5% by weight and preferably 0.1 to 3% by weight, expressed as active dyeing ingredient relative to the total weight of the composition.

The dyestuffs according to the invention can be used individually or in a mixture, in, for example, liquid compositions which have been thickened to a greater or lesser extent, or in compositions presented in the form of creams, gels or oils, or in powders to be diluted with a liquid at the time of use.

They can also be used in association with other direct dyestuffs. One of the preferred forms of the invention is the use of the dyestuffs of the formula (I) in conjunction with direct dyestuffs, and more particularly with natural dyestuffs such as lawsone or powdered henna leaves.

In the latter case, one of the particularly preferred embodiments of the compositions according to the invention consists of the presentation in the form of a poultice. In this case, the 2-hydroxy-1,4-naphthoquinones used in this invention, and preferably the 2-hydroxy-1,4-naphthoquinones of natural origin, which can adopt the various forms mentioned above, are prepared in the forms of powders which are stable on storage and introduced into a solid medium which can be composed of powder, flour or starchy or mucilaginous substances, and which is diluted with an appropriate liquid at the time of use so as to form a mixture having a suitable consistency for application to the hair.

The powders used in compositions of this type, which are also called "poultices", can consist of insoluble substances such as silicas, plants, clays, plants powdered after solvent extraction of their active principles, or also plants or animals containing the 2-hydroxy-1,4-naphthoquinones according to the invention. The liquid used to dilute the powder can consist of water and/or a cosmetically acceptable solvent such as an alcohol, glycol or oil. The viscosity generally obtained after mixing should be from 300 to 5,000 centipoises.

The cosmetically acceptable medium for the other embodiments of the dyeing compositions for human hair, according to the invention, is generally aqueous and its pH is suitably from 2 to 11 and can be adjusted to the desired value with alkalising agents or acidifying agents.

These compositions can also contain anionic, cationic, non-ionic or amphoteric surface-active agents or mixtures thereof. Amongst the preferred surface-active agents, there may be mentioned, more particularly, soaps, alkylbenzenesulphonates, alkylnaphthalenesulphonates, fatty alcohol sulphates, ether-sulphates or sulphonates, quaternary ammonium salts, fatty acid diethanolamides, polyoxyethyleneated or polyglycerolated acids, alcohols or amides, and polyoxyethyleneated or polyglycerolated alkylphenols. The surface-active agents are suitably present in the compositions according to the invention in an amount from 0.1 to 55% by weight and preferably from 1 to 40% by weight, relative to the total weight of the composition.

These compositions can also contain organic solvents; examples of these which may be mentioned are lower alkanols such as ethanol and isopropanol, polyols such as glycerol, glycols or glycol ethers, such as ethylene glycol, propylene glycol, ethylene glycol monobutyl ether and diethylene glycol monoethyl ether and monomethyl ether, and also analogous products or mixtures thereof. These solvents are preferably used in amounts from 1 to 60% by weight and more particularly from 3 to 30% by weight, relative to the total weight of the composition.

The compositions can also contain anionic, non-ionic, cationic or amphoteric polymers, or a mixture thereof, in amounts from, say, 0.1 to 5% by weight.

The compositions according to the invention can be thickened, preferably with compounds chosen from amongst sodium alginate, gum arabic, guar gum or carob gum, pectins, cellulose derivatives such as methyl-cellulose, hydroxymethylcellulose, hydroxypropylmethylcellulose or carboxymethylcellulose, and various polymers serving this purpose, such as acrylic acid derivatives. It is also possible to use inorganic thickeners such as bentonite. These thickeners are preferably present in amounts of 0.1 to 5% by weight and in particular of 0.5 to 3% by weight, relative to the total weight of the composition.

Any other adjuvants normally used in dyeing compositions for the hair, such as penetrating agents, sequestering agents, antioxidants, buffers and perfumes, can also be added to the compositions according to the invention.

If the compositions contain other direct dyestuffs, these are generally present in an amount from 0.005 to 10% by weight.

The process for dyeing human keratin fibres, in particular human hair, according to the invention, is essentially characterised in that at least one composition such as defined above is applied to the human keratin fibres, and in particular to the hair, before or after shampooing, it is left for, say, 5 to 60 minutes and preferably 5 to 40 minutes, and the said fibres are rinsed, washed, if desired, and dried. A composition in the form of a setting lotion can also be applied to the hair, after shampooing, and the hair is then dried.

The dyeing of human keratin fibres, and in particular of the hair, can also be carried out by multistep processes, at least one step consisting in applying a dyestuff of the formula (I). These multistep processes make it possible, in particular, to employ compositions having different pH values according to the nature of the dyestuffs present.

The following Examples further illustrate the present invention.

EXAMPLES 1 TO 12

For each of Examples 1 to 12, the following dyeing composition is prepared:

| | |
|---|---|
| Powdered extraction residue of saponaria | 35 g |
| Powdered maize cobs | 15 g |
| Citric acid | 4 g |
| Vidogum L175 sold by UNIPECTINE | 3 g |
| Dyestuff | 2 g |
| Skimmed milk powder q.s. | 100 g |

This composition is mixed with three times its weight of warm water, and the poultice thus obtained is applied to 90% white hair which may or may not have been permed.

After an application time of 30 minutes, the mixture is removed by rinsing. The hair is subsequently washed and then dried.

The table which follows gives the dyeing results according to the nature of the dyestuff used.

TABLE II

| Example No. | Dyestuff | Dyeing result |
|---|---|---|
| 1 | 2,5-Dihydroxy-1,4-naphthoquinone | intense reddish copper |
| 2 | 2,6-Dihydroxy-1,4-naphthoquinone | golden copper |
| 3 | 2,7-Dihydroxy-1,4-naphthoquinone | intense reddish copper |
| 4 | 2,8-Dihydroxy-1,4-naphthoquinone | intense copper |
| 5 | 2,3,5-Trihydroxy-1,4-naphthoquinone | pinkish copper |
| 6 | 2,5,7-Trihydroxy-1,4-naphthoquinone | intense purplish red |
| 7 | 2,6,7-Trihydroxy-1,4-naphthoquinone | pinkish beige |
| 8 | 2,3,5,8-Tetrahydroxy-1,4-naphthoquinone | greyish beige |
| 9 | 2-Hydroxy-3-methoxy-1,4-naphthoquinone | intense purplish red |
| 10 | 2-Hydroxy-5-methoxy-1,4-naphthoquinone | golden copper |
| 11 | 2-Hydroxy-8-methoxy-1,4-naphthoquinone | intense golden |
| 12 | 2,3-Dihydroxy-6-methoxy-1,4-naphthoquinone | pinkish beige |

EXAMPLES 13 TO 28

For each of Examples 13 to 28, the following dyeing composition is prepared:

| | |
|---|---|
| Powdered extraction residue of saponaria | 30 g |
| Powdered maize cobs | 50 g |
| Sodium carbonate | 3 g |
| Dyestuff | 2 g |
| Skimmed milk powder q.s. | 100 g |

This composition is mixed with three times its weight of warm water, and the poultice thus obtained is applied to 90% white hair which may or may not have been permed.

After an application time of 30 minutes, the mixture is removed by rinsing. The hair is subsequently washed and then dried.

The table which follows gives the dyeing results according to the nature of the dyestuff used in the composition.

TABLE III

| Example No. | Dyestuff | Dyeing result |
|---|---|---|
| 13 | 2,3-Dihydroxy-1,4-naphthoquinone | greyish blue |
| 14 | 2,5-Dihydroxy-1,4-naphthoquinone | intense reddish copper |
| 15 | 2,6-Dihydroxy-1,4-naphthoquinone | beige copper |
| 16 | 2,7-Dihydroxy-1,4-naphthoquinone | reddish copper |
| 17 | 2,5,7-Trihydroxy-1,4-naphthoquinone | purplish red |
| 18 | 2,6,7-Trihydroxy-1,4-naphthoquinone | beige |
| 19 | 2,3,5,8-Tetrahydroxy-1,4-naphthoquinone | greyish mauve |
| 20 | 2-Hydroxy-3-methoxy-1,4-naphthoquinone | purplish red |
| 21 | 2-Hydroxy-5-methoxy-1,4-naphthoquinone | copper |
| 22 | 2-Hydroxy-6-methoxy-1,4-naphthoquinone | copper |
| 23 | 2-Hydroxy-7-methoxy-1,4-naphthoquinone | pinkish copper |
| 24 | 2-Hydroxy-8-methoxy-1,4-naphthoquinone | intense golden |
| 25 | 2,3-Dihydroxy-5-methoxy-1,4-naphthoquinone | greenish grey |
| 26 | 2,3-Dihydroxy-6-methoxy-1,4-naphthoquinone | beige |
| 27 | 2,8-Dihydroxy-3-methyl-1,4-naphthoquinone | medium purplish red |
| 28 | 2-Hydroxy-3-nitro-7-methoxy-1,4-naphthoquinone | golden |

EXAMPLE 29

The following composition is prepared:

| | |
|---|---|
| 2-Hydroxy-3-methoxy-1,4-naphthoquinone | 0.8 g |
| 2,5-Dihydroxy-1,4-naphthoquinone | 0.55 g |
| Cetyl alcohol | 17.0 g |
| MERGITAL CS 15 E | 6 g |
| Oleyl alcohol | 3.0 g |
| Citric acid q.s | pH 2.3 |
| Distilled water q.s. | 100 g |

This composition is in the form of a cream, which is applied to a chestnut head of hair for 30 minutes. After rinsing and shampooing, the dried hair has a coppery red sheen.

EXAMPLE 30

The following composition is prepared:

| | |
|---|---|
| 2-Hydroxy-8-methoxy-1,4-naphthoquinone | 0.05 g |
| Vinyl acetate/crotonic acid copolymer (90/10) | 1.8 g |
| Vinylpyrrolidone/vinyl acetate copolymer (60/40) | 0.4 g |
| 96° strength ethyl alcohol q.s. | 50° alcoholic strength |
| Triethanolamine q.s. | pH 6 |
| Distilled water q.s | 100 g |

This setting lotion is applied to natural light blond hair. After drying, the head of hair is coloured a golden light blond shade.

EXAMPLE 31

The following composition is prepared:

| | |
|---|---|
| 2,3-Dihydroxy-1,4-naphthoquinone | 0.6 g |
| 2-Amino-4-methyl-5-N—(β-hydroxyethyl)-amino-nitrobenzene | 0.15 g |
| SACTIPON 8533 | 20 g |
| 2-Ethoxyethanol | 10 g |
| 2-(N,N-Dimethylamino)-ethanol q.s. pH | 9.6 |
| Distilled water q.s | 100 g |

This shampoo is used for dyeing a deep chestnut head of hair. After an application time of 20 minutes, rinsing and drying, hair having a purple-violet sheen is obtained.

EXAMPLE 32

The following composition is prepared:

| | |
|---|---|
| 2-Hydroxy-7-methoxy-1,4-naphthoquinone | 0.35 g |
| Cetyl alcohol | 17.0 g |
| MERGITAL CS 15 E | 6.0 g |
| Oleyl alcohol | 3.0 g |
| Citric acid q.s | pH 3 |
| Distilled water q.s. | 100 g |

This cream is applied to a very light blond head of hair. After an application time of 30 minutes, rinsing and shampooing, the dried hair has a golden beige sheen.

EXAMPLE 33

The following composition is prepared:

| | |
|---|---|
| 2,3-Dihydroxy-1,4-naphthoquinone | 1.0 g |
| 2,5,7-Trihydroxy-1,4-naphthoquinone | 0.6 g |
| Lanette wax 0 | 20.0 g |
| Stearyldimethylamine oxide at a concentration of 25% in water | 12.0 g |
| Ammonium lauryl-sulphate containing 20% of fatty alcohol | 10.0 g |
| 2-(N,N—Dimethylamino)-ethanol q.s. | pH 9.5 |
| Distilled water q.s. | 100 g |

This cream is applied to brown hair for 30 minutes. After rinsing, the hair is shampooed. The hair is dried. It has a midnight blue sheen.

EXAMPLE 34

The following composition is prepared:

| | |
|---|---|
| 2,6,7-Trihydroxy-1,4-naphthoquinone | 0.05 g |
| 2,6-Dihydroxy-1,4-naphthoquinone | 0.05 g |
| Vinyl acetate/crotonic acid copolymer (90/10) | 1.8 g |
| Vinylpyrrolidone/vinyl acetate copolyer (60/40) | 0.4 g |
| 96° strength ethyl alcohol q.s. | 50° alcoholic strength |
| Triethanolaine q.s. | pH 5 |
| Distilled water q.s. | 100 g |

This composition constitutes a setting lotion, which is applied to blond hair. After drying and shaping, the head of hair is coloured a blond shade with a beige sheen.

EXAMPLE 35

The following composition is prepared:

| | |
|---|---|
| 2,5,7-Trihydroxy-1,4-naphthoquinone | 0.5 g |
| 2-Hydroxy-1,4-naphthoquinone | 0.1 g |
| Cetyl alcohol | 17.0 g |
| MERGITAL CS 15 E | 6.0 g |
| Oleyl alcohol | 3.0 g |
| Citric acid q.s. | pH 2 |

| | |
|---|---|
| -continued | |
| Distilled water q.s. | 100 g |

This cream is applied to a light chestnut head of hair. After an application time of 30 minutes, rinsing, washing and drying, the hair is shaded with an intense coppery brown sheen.

EXAMPLE 36

The following composition is prepared:

| | |
|---|---|
| 2,3,5-Trihydroxy-1,4-naphthoquinone | 0.5 g |
| Cetyl alcohol | 17.0 g |
| MERGITAL CS 15 E | 6.0 g |
| Oleyl alcohol | 3.0 g |
| Citric acid q.s. | pH 2 |
| Distilled water q.s. | 100 g |

This cream is applied for 30 minutes to a deep blond head of hair containing a fairly high percentage of white hair. The hair is rinsed, washed and dried. The hair is then restored to its natural shade and the white hair is covered in the same colour.

EXAMPLE 37

The following composition is prepared:

| | |
|---|---|
| 2,3-Dihydroxy-1,4-naphthoquinone | 1 g |
| 2-N—Methylamino-4-($\beta\Gamma$-dihydroxypropoxy)-nitrobnzene | 0.7 g |
| Lanette wax 0 | 20.0 g |
| Stearyldiethylamine oxide at a concentration of 25% in water | 12.0 g |
| Ammonium lauryl-sulphate containing 20% of fatty alcohol | 10.0 g |
| 2-(N,N—Dimethylamino)-ethanol q.s. | pH 9.2 |
| Distilled water q.s. | 100 g |

This composition, which is in the form of a cream, is applied for 30 minutes to a chestnut head of hair with a warm sheen. After rinsing, shampooing and drying, the hair has regained a more natural shade of duller character.

The tradenames denote the following products:

| | |
|---|---|
| MERGITAL CS 15E | Cetyl/stearyl alcohol oxyethyleneated with 15 mols of ethylene oxide, sold by HENKEL. |
| SACTIPON 8533 | Sodium salt of sulphated oxyethyleneated alkanol, containing 0.6 milli-equivalent/g, sold by LEVER. |
| LANETTE WAX 0 | 50/50 mixture of cetyl alcohol and stearyl alcohol, sold by HENKEL. |

We claim:

1. A composition suitable for dyeing human hair, which comprises, in a cosmetically acceptable medium, about 0.01 to 5% of at least one 2-hydroxy-1,4-naphthoquinone of the formula:

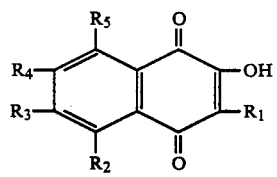

in which $R_1$ denotes a hydrogen or halogen atom, or a hydroxy, alkoxy, nitro, alkyl or acyl group, and $R_2$, $R_3$, $R_4$ and $R_5$ independently of one another denote hydrogen or a hydroxy, alkoxy, alkyl or acyl group, such that at least one of the substituents $R_1$ to $R_5$ is other than hydrogen, and if $R_1$, $R_3$ and $R_4$ denote hydrogen, $R_2$ and $R_5$ cannot simultaneously denote hydroxy, said alkyl and alkoxy groups for $R_1$, $R_2$, $R_3$, $R_4$ and $R_5$ containing 1-4 carbon atoms and said acyl group for $R_1$, $R_2$, $R_3$, $R_4$ and $R_5$ containing 2-4 carbon atoms, said medium containing adjuvants suitable for use for hair dyeing.

2. Process for dyeing human hair which comprises applying thereto at least one composition as defined in claim 1,
allowing said composition to remain on the hair for 5 to 60 minutes, and
drying said hair.

3. Process for dyeing human hair which comprises applying thereto at least one 2-hydroxy-1,4-naphthoquinone of formula (I) as defined in claim 1.

4. A composition suitable for dyeing human hair, which comprises in a cosmetically acceptable medium about 0.1 to 5% of at least one 2-hydroxy-1,4-naphthoquinone of the formula

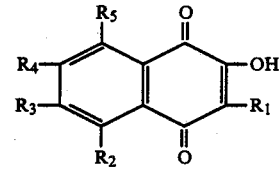

in which $R_1$ is selected from the group consisting of hydrogen, halogen, hydroxy, alkoxy, nitro, alkyl and acyl, and $R_2$, $R_3$, $R_4$ and $R_5$ independently of one another are hydrogen, hydroxy, alkoxy, alkyl or acyl, such that at least one of the substituents $R_1$ to $R_5$ is other than hydrogen, and if $R_1$, $R_3$ and $R_4$ are hydrogen, $R_2$ and $R_5$ cannot simultaneously denote hydroxy, said alkyl and alkoxy groups for $R_1$, $R_2$, $R_3$, $R_4$ and $R_5$ containing 1-4 carbon atoms and said acyl group for $R_1$, $R_2$, $R_3$, $R_4$ and $R_5$ containing 2-4 carbon atoms,
said composition being in the form of a lotion, a thickened liquid, a cream, a gel, an oil or a powder intended to be diluted at the time of use with a liquid selected from the group consisting of water, an alcohol, a glycol, an oil, mixtures of water and alcohol, mixtures of water and glycol, and mixtures of water and oil.

5. A composition according to claim 1, wherein:
said cosmetically acceptable medium is selected from the group consisting of water, and a mixture of water and a solvent, said solvent being selected from the group consisting of lower alkanols, glycerol, glycols, and glycolethers, said solvent being present in an amount between 1 and 60% by weight, and further comprising:
a surface-active agent selected from the group consisting of anionic, cationic, non-ionic and amphoteric surface-active agents and mixtures of anionic, cationic, non-ionic and amphoteric surface-active agents, said surface active agents appearing in an amount between 0.1 and 55% by weight, the pH of said composition being between 2 and 11.

6. A composition according to claim 4, wherein:

said cosmetically acceptable medium is selected from the group consisting of water, and a mixture of water and a solvent, said solvent being selected from the group consisting of lower alkanols, glycerol, glycols, and glycolethers, said solvent being present in an amount between 1 and 60% by weight, and further comprising:

a polymer being selected from the group consisting of anionic, non-ionic, cationic, and amphoteric polymers, said polymer being present in an amount of 0.1 to 5% by weight.

7. A composition according to claim 4, wherein: said cosmetically acceptable medium is selected from the group consisting of water, and a mixture of water and a solvent, said solvent being selected from the group consisting of lower alkanols, glycerol, glycols, and glycolethers, said solvent being present in an amount between 1 and 60% by weight, and further comprising:

a thickening agent in an amount of 0.1 to 5% by weight.

8. The composition of claim 7 having a pH of from 2 to 11.

9. The composition of claim 6 having a pH of about 2 to 11.

10. A composition according to claim 4 in which $R_1$ denotes a hydrogen or bromo atom or a hydroxy, methyl, ethyl, methoxy or acetyl radical and at least one of $R_2$ to $R_5$ represents a hydrogen atom or a hydroxy, methoxy, ethyl or acetyl radical.

11. A composition according to claim 10 in which the dyestuff is 2,3-dihydroxy-1,4-naphthoquinone, 2,5-dihydroxy-1,4-naphthoquinone, 2,6-dihydroxy-1,4-naphthoquinone, 2,7-dihydroxy-1,4-naphthoquinone, 2,8-dihydroxy-1,4-naphthoquinone, 2,5,7-trihydroxy-1,4-naphthoquinone, 2,6,7-trihydroxy-1,4-naphthoquinone, 2-hydroxy-3-methoxy-1,4-naphthoquinone, 2-hydroxy-5-methoxy-1,4-naphthoquinone, 2-hydroxy-6-methoxy-1,4-naphthoquinone, 2-hydroxy-7-methoxy-1,4-naphthoquinone, 2-hydroxy-8-methoxy-1,4-naphthoquinone, 2,3,5-trihydroxy-1,4-naphthoquinone, 2,3,5,8-tetrahydroxy-1,4-naphthoquinone, 2,3-dihydroxy-7-methoxy-1,4-naphthoquinone, 2,8-dihydroxy-3-methyl-1,4-naphthoquinone, 2-hydroxy-3-nitro-7-methoxy-1,4-naphthoquinone, 2-hydroxy-3-methyl-1,4-naphthoquinone or 2,3-dihydroxy-5-methoxy-1,4-naphthoquinone.

12. A composition according to claim 10 which contains a dyestuff selected from the group consisting of:
2,5,6,7-tetrahydroxy-1,4-naphthoquinone,
2,5,7,8-tetrahydroxy-1,4-naphthoquinone,
2,5,6,7,8-pentahydroxy-1,4-naphthoquinone,
2-hydroxy-5,8-dimethoxy-1,4-naphthoquinone,
2-hydroxy-5,6,7-trimethoxy-1,4-naphthoquinone,
2-hydroxy-5,7,8-trimethoxy-1,4-naphthoquinone,
2-hydroxy-5,6,7,8-tetramethoxy-1,4-naphthoquinone,
2-hydroxy-3-bromo-1,4-naphthoquinone,
2,5,8-trihydroxy-6-ethyl-1,4-naphthoquinone,
2,5,7-trihydroxy-6-acetyl-1,4-naphthoquinone,
2,5,8-trihydroxy-6-acetyl-1,4-naphthoquinone and
2,5,7,8-tetrahydroxy-3-acetyl-1,4-naphthoquinone.

13. A composition according to claim 4, in which the dyestuff is of natural origin.

14. A composition according to claim 4, which comprises at least one 2-hydroxy-1,4-naphthoquinone of formula (I) in the form of a powder which is stable on storage, and a solid medium which is a powder selected from the group consisting of silicas, plants, clays and plants powdered after solvent extraction of their active principle, flour or a starchy or mucilagenous substance, said composition being intended to be diluted at the time of use with an amount of said liquid suitable to form a mixture having a viscosity of 300 to 5000 centipoises.

15. A composition according to claim 4, further comprising:
at least one direct dyestuff other than 2-hydroxy-1,4-naphthoquinone of the formula (I), said other direct dyestuff being present in an amount of between about 0.005 to about 10% by weight of the composition.

16. Process for dyeing human hair, which comprises applying thereto a composition as claimed in claim 14 after said composition has been diluted with said liquid at the time of use.

* * * * *